United States Patent [19]
Mitchell et al.

[11] 4,382,384
[45] May 10, 1983

[54] ACOUSTIC PENETROMETER FOR SUBSOIL INVESTIGATION

[75] Inventors: James K. Mitchell, Moraga; Willem C. B. Villet, Berkeley; Philip T. Tringale, Moraga; Clarence K. Chan, San Francisco, all of Calif.

[73] Assignee: The Regents of The University of California, Berkeley, Calif.

[21] Appl. No.: 273,946

[22] Filed: Jun. 15, 1981

[51] Int. Cl.³ .................. G01N 19/02; G01N 3/42
[52] U.S. Cl. .................................... 73/594; 73/84
[58] Field of Search ............... 73/84, 573, 587, 594

[56] References Cited
U.S. PATENT DOCUMENTS

| | | | |
|---|---|---|---|
| 2,790,968 | 4/1957 | Cook et al. | 73/573 |
| 3,906,781 | 9/1975 | Vlasblom | 73/84 |

Primary Examiner—S. Clement Swisher
Attorney, Agent, or Firm—Owen, Wickersham & Erickson

[57] ABSTRACT

A quasi-static cone penetrometer for subsoil investigation by simultaneously generating three sets of data, namely cone tip penetration resistance, sleeve friction resistance, and acoustical information, all as a function of depth. The penetrometer has a substantially smooth cylindrical outer surface terminating in a cone tip. The lower portion of the smooth cylindrical outer surface is provided by a friction sleeve immediately above the cone tip insulated from it by acoustic attenuation means. A microphone in the tip (or elsewhere in the penetrometer) is responsive to acoustical input generated, for example, by the tip moving through the soil, and sound barrier means holds said microphone firmly in place. The sound barrier means, the acoustic attenuation means, and the acoustical dampening means substantially isolate the microphone from the core ring and from the friction sleeve. A tip load cell is joined to the cone tip and insulated from it acoustically by acoustical-dampening means. A friction load cell has its upper end connected to the tip load cell and the remainder spaced away from it, while its lower end is secured to the friction sleeve.

22 Claims, 14 Drawing Figures

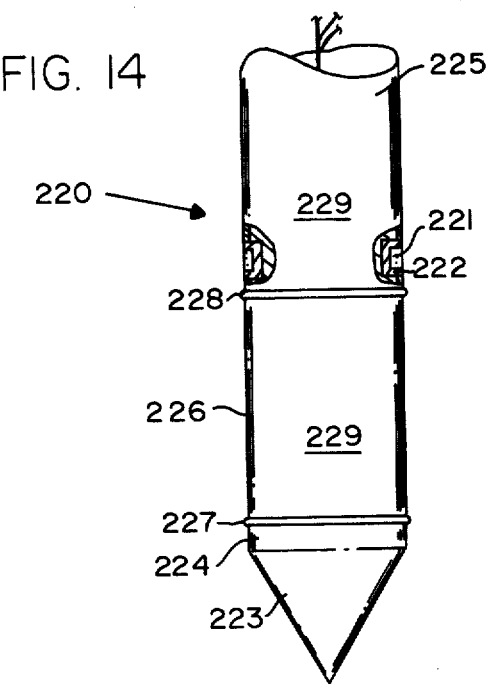
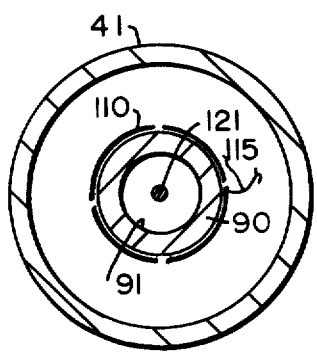
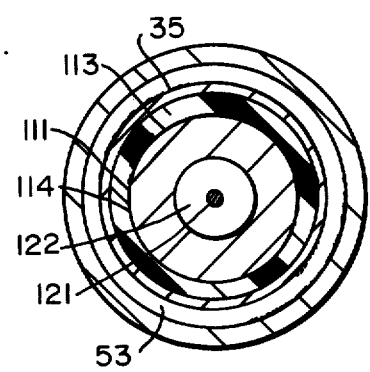
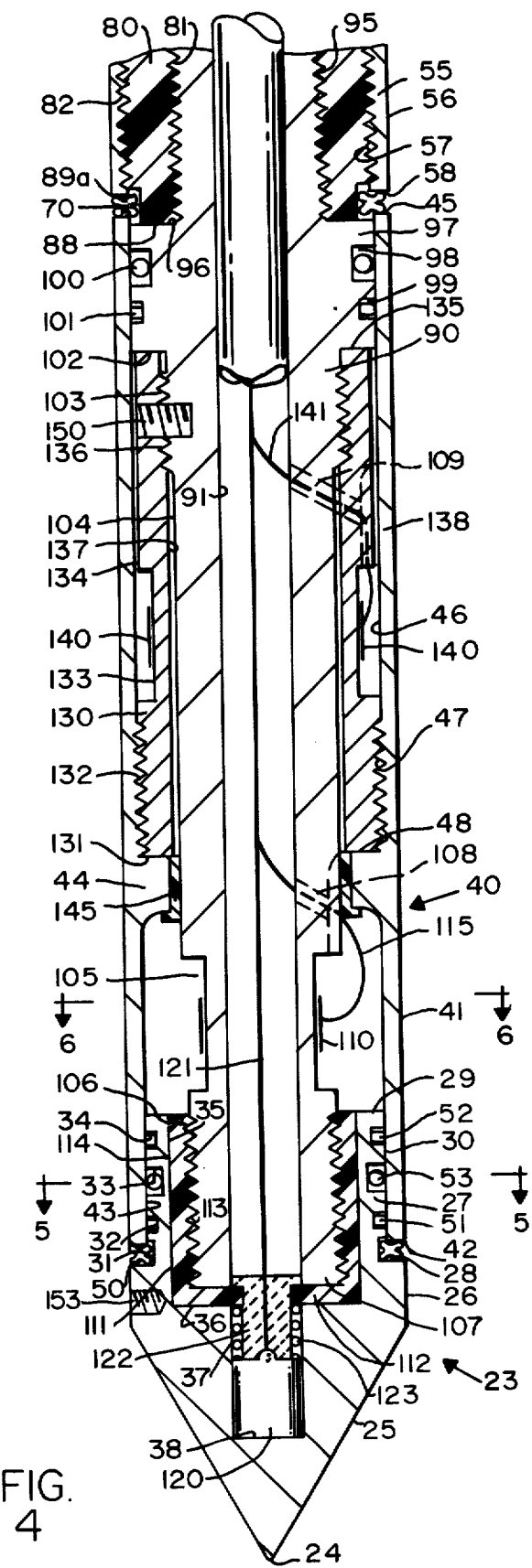
FIG. 14
FIG. 6
FIG. 5
FIG. 4

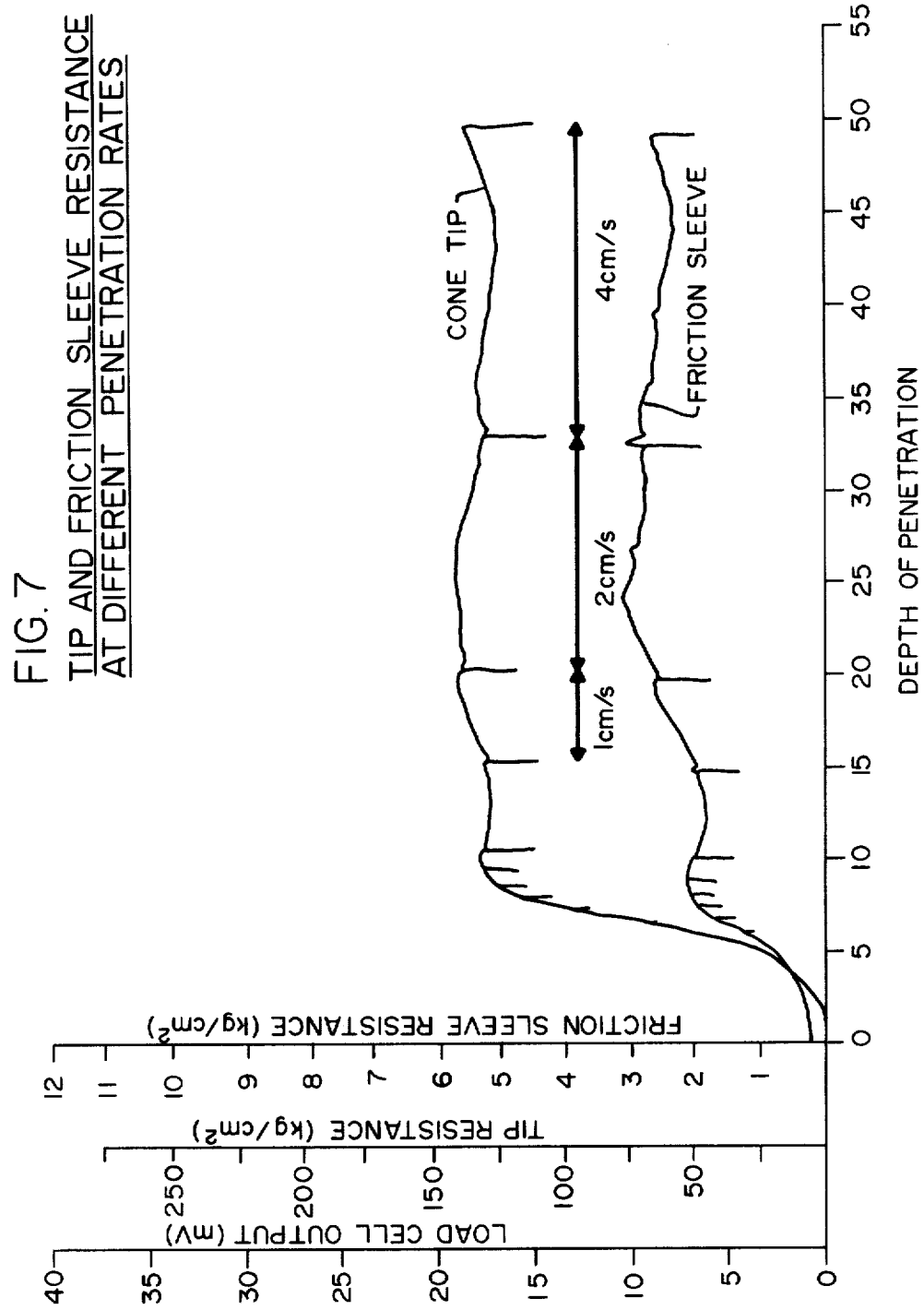

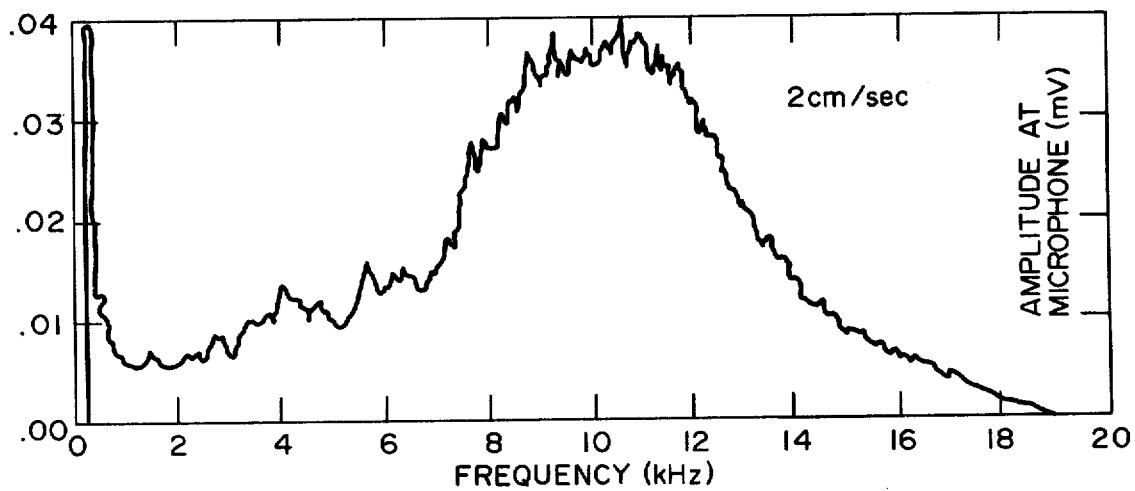
FIG.8 FREQUENCY DISTRIBUTION CURVE OF THE ACOUSTIC SIGNAL GENERATED DURING STATIC CONE PENETRATION OF A SAND
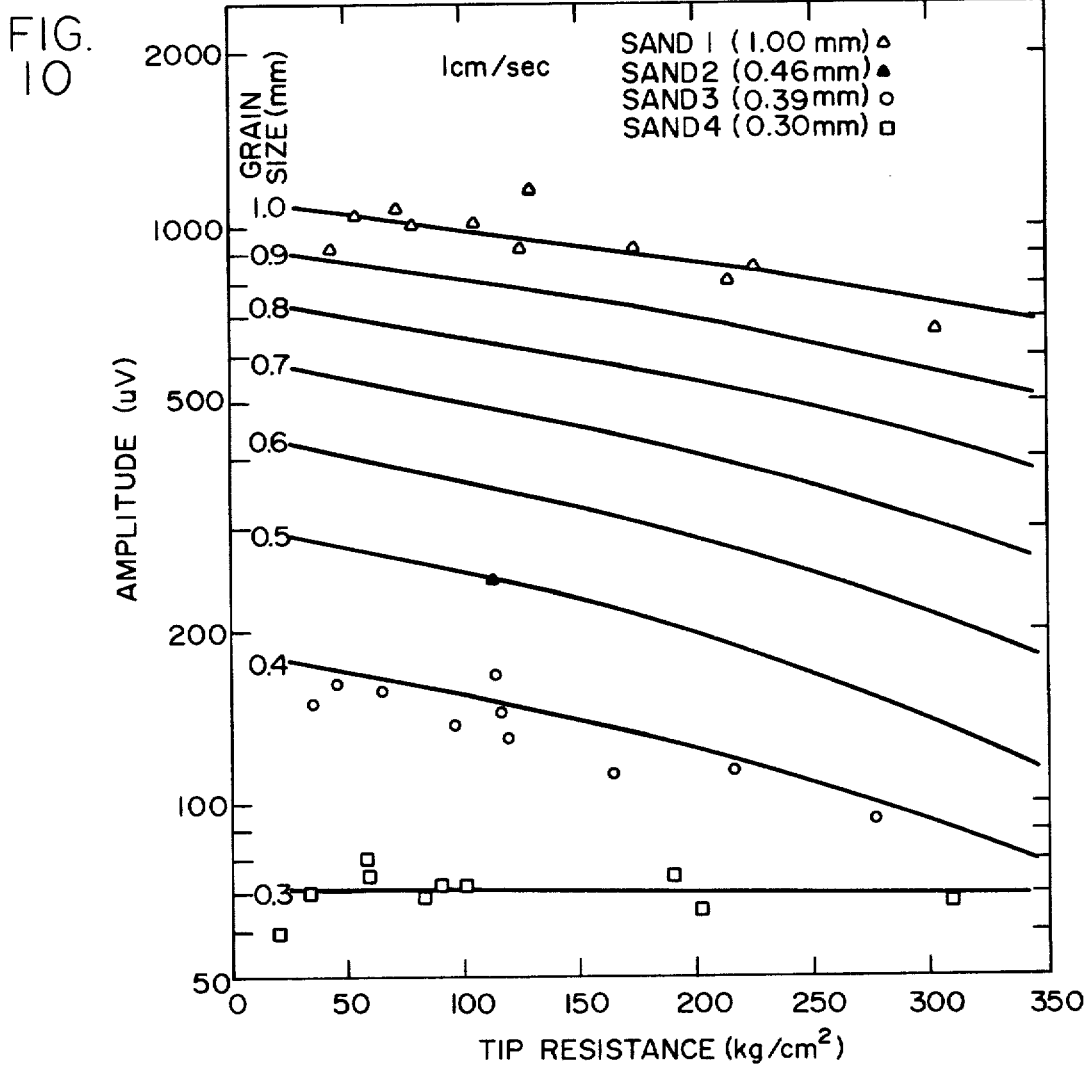
FIG. 10

FREQUENCY DISTRIBUTION CURVES
EXPANDED VERTICAL SCALES

CONE TIP RESISTANCE, & PEAK TO PEAK VOLTAGE OF THE ACOUSTIC SIGNAL AS A FUNCTION OF DEPTH AT A PENETRATION RATE OF 4 cm/s

ACOUSTIC PENETROMETER FOR SUBSOIL INVESTIGATION

The Government has rights in this invention pursuant to Grant No. ENG 77-20933 awarded by the National Science Foundation.

This invention relates to a quasi-static cone penetrometer for subsoil investigation by simultaneously generating three sets of data which are continuously recorded with depth. These data are: (1) cone tip resistance, (2) friction sleeve resistance, and (3) acoustical information generated by interaction between the device and the soil. It also relates to soil investigative apparatus and method.

BACKGROUND OF THE INVENTION

Quasi-static cone penetrometers of various types have heretofore been used extensively to determine the engineering properties of various soils, whether they be clays, sands, or loams. The principal measurement has been the resistance to penetration of the penetrometer into the soil at a constant velocity. The penetrometer has typically been a standard cone-tipped cylindrical shaft with apparatus for measuring tip resistance, such data being recorded against depth. A limitation of such penetrometers heretofore has been that the type of soil being penetrated was not always readily identified and that such identification is requisite for successful interpretation of the tip resistance data.

It has been found that the amount of frictional resistance to penetration of a smooth cylindrical sleeve that is above and connected to the penetrometer cone tip is also useful in understanding the soil characteristics and thus for geotechnical design. This, too, can be measured by the same instrument when it is provided with additional apparatus.

Until recently, a so-called friction ratio, obtained by dividing the measured frictional resistance by the measured tip resistance, has been the principal method by which attempts were made to distinguish different soil types from one another during penetration testing. Such distinction of soil type, however, is possible only between sands and clays, and is not considered to be reliable, even for those widely different grain sizes. For example, research has shown that four sands identical in all aspects except for differing in the important parameter of grain size, yielded essentially identical "friction ratios"; it would therefore not be possible to distinguish between the four sands on the basis of friction ratio.

A device able to generate these two types of data may comprise a cone tip with a tip load cell, a friction sleeve above the tip with a friction load cell, and a common shaft above the tip threaded to the tip load cell and to the friction sleeve load cell. Leads from the load cells pass up through a hollow core of the common shaft to the upper end of the penetrometer and thence through penetrometer rods to the ground surface and to suitable recording apparatus.

Frictional resistances are also required for the design of friction piles. The adhesion of soil to the smooth metal jacket of the friction sleeve, may not necessarily be identical to the adhesion of the soil to a concrete, wood or rough iron pile; the measured friction resistance on the smooth friction sleeve is, however, a very good indicator of what the magnitudes of such adhesion may be.

It has been determined that as a rigid object, such as a penetrometer, is pushed into a soil, acoustic emissions are generated by soil grains sliding and rolling over one another, sliding and rolling over the penetrating object, and being crushed. Little use of such acoustic emissions has heretofore been made, and none, so far as we are aware, in a penetrometer which can transmit such acoustic emissions simultaneously with the measurement of cone tip penetration resistance and friction sleeve resistance. Such acoustical response is, in this invention, detected by an acoustical transducer located within the penetrometer and recorded on magnetic tape as well as being amplified for direct listening during the penetration tests.

We have found that a greatly improved identification in situ of soil types and strata boundaries, can be obtained by simultaneously obtaining and recording all three types of data.

In order to do this in an optimum manner one must solve the problem of preventing the noise generated by soil grains moving over the friction sleeve from interfering with and modifying the acoustical data generated by the grains moving over the conical tip. In other words, one must so isolate the acoustic tip that it does not receive acoustic information from the remainder of the penetrometer and its associated rods.

Acoustical emissions generated by soil penetration

In previous geotechnical engineering applications in which acoustic emissions in geologic deposits were monitored, the process could in most instances be considered passive, for the electromechanical transducers utilized for such monitoring responded to mostly subaudible elastic waves which were generated when the deposit was deformed as a result of ground movements induced by causes not related to the transducer. Once installed, the transducers were not the source of deformation, and consequently not of the acoustic emissions either; hence, the description of the monitoring process as passive.

In the present invention an active approach is used wherein the interaction between the monitoring equipment and a soil deposit is the source of acoustic emissions. As the penetrometer is pushed into the soil, acoustic emissions are generated by soil grains sliding and rolling over the penetrating object, sliding and rolling over one another, and being crushed. For a given penetrometer advancing at a steady rate, the nature of such emissions is determined by, at least:
 (1) The nature of the penetrating object.
 (2) The rate of advance of the penetrating object.
 (3) The nature of the soil, which includes:
   (a) Soil particle characteristics such as grain size, grain shape, grain hardness, grain surface texture or coating, grain strength.
   (b) Particle size distribution.
   (c) Grain arrangment (fabric).
   (d) Confining stress.
   (e) Density (void ratio).
 (4) The state of saturation of the soil.

For a given penetrating object advancing at a given rate of penetration, the quality of the sound is determined by at least some of the factors stated in (3) and (4) above, which factors are important in determining the engineering properties of the soil.

By supplementing the usual penetration resistance data with simultaneously obtained acoustical data, more certain soil identification and property interpretations become possible.

In initial experiments the inventors investigated the potential usefulness of such acoustical emissions by amplifying and listening to the sounds produced when a miniature cone penetrometer was pushed into jars containing various soils. Distinct differences were audible not only between the sounds produced by sands and clays, but also among those sounds produced by sands of different grain sizes.

A penetrometer embodying one form of the invention was then made using a guitar pick-up microphone within a penetrometer cone. The cone base cross-sectional area was 10 cm$^2$, while the tip apex angle was 60°. This acoustic cone was pushed into containers filled with sands of various gradations. For each sand, tests were performed at various densities with penetration rates of 0.25, 0.5, 1, and 2 centimeters per second. For some materials, a penetration rate of 4 centimeters per second was also employed. The output of the microphone was recorded, plotted by means of an oscillograph, and analyzed with a spectrum analyzer.

These analyses indicated that sufficient differences existed among the various signals to justify a systematic and detailed investigation that could culminate in the development of improved penetrometers incorporating acoustical data acquisition devices. Since then, the results of such an investigation have already demonstrated the usefulness of the method for its intended purpose. Studies of the acoustic noise associated with the shearing and straining of soils, have shown amplitudes and rates of the acoustic emissions to be dependent on grain size and state of saturation. Acoustic emissions during strain in sands, for instance, have amplitudes about 400 times higher than those in clays.

SUMMARY OF THE INVENTION

The invention comprises, first, a quasi-static cone penetrometer for subsoil investigation. Three sets of data are generated simultaneously, namely cone tip penetration resistance, friction sleeve resistance, and acoutical information, all as functions of depth of penetration.

The penetrometer comprises a body assembly, preferably with a substantially smooth cylindrical outer surface which terminates in a cone at its lower end. The cone tip preferably has a 60° vertex angle, its conical outer surface extending upwardly from the vertex to the smooth cylindrical outer surface. Above the cone tip is a friction sleeve having an outer surface forming part of the smooth cylindrical outer surface. Preferably, means for acoustic attenuation between the cone tip and the friction sleeve substantially insulates them acoustically from each other.

Inside this shell is a core ring having an inner bore and a load cell portion where tip-responsive strain gauges are mounted. In the present invention, this core ring is preferably not connected directly to the cone tip. Instead, acoustical-dampening means is interposed between the cone tip and the core ring, insulating them acoustically from each other while yet transmitting to the strain gauges the resistance of the soil to the movement of the tip into the soil.

The friction load cell is located in an intermediate sleeve around the core ring and inside the friction sleeve. The upper end of the friction load cell is connected to the core ring, the remainder being spaced away from it. The lower end of the friction load cell is secured to the friction sleeve. This intermediate sleeve has friction strain gauges responsive to the friction between the friction sleeve and the soil.

In the present invention there is also a microphone. This microphone may be in the cone tip, responsive to the acoustical input generated by the tip moving through the soil. The microphone is held firmly in place in the cone tip. Sound barrier means is located between the microphone and the hollow core. The sound barrier means and the acoustic attenuation or dampening means substantially isolate the microphone from the core ring and the friction sleeve. Leads from each of the load cells and from the microphone extend up through the bore of the core ring to the upper end of the penetrometer.

The body assembly typically includes additional shell portions or "rods" continuing the smooth cylindrical outer surface of the body upwardly from the friction sleeve. In this invention, an annular acoustical dampening member is interposed between those shell portions and the core ring.

A data acquisition system is combined with this penetrometer. Tip resistance, friction sleeve resistance and the amplitude of the acoustic signal are thereby recorded versus depth of penetration. An oscilloscope gives visual depiction of the acoustic signal, which is amplified, listened to, and also recorded, preferably by a tape recorder, which may simultaneously record the data relevant to depth of penetration and the resistances of the tip and friction sleeve.

The method of the insertion involves penetrating the soil while listening, recording, and observing the resultant signals in order to obtain information about the characteristics of the subsoil.

Other features, objects, and advantages of the invention will appear from the following description of a preferred embodiment thereof.

BRIEF DESCRIPTION OF THE DRAWINGS

FIG. 4 is an enlarged view in section of the lower portion of FIG. 2.

FIG. 5 is a view in section taken along the line 5—5 in FIG. 4.

FIG. 6 is a view in section taken along the line 6—6 in FIG. 4.

FIG. 7 is a chart of one test wherein load cell outputs for tip resistance and friction sleeve resistance are plotted for three different penetration rates in the same sample material.

FIG. 8 is a frequency distribution curve of the acoustic signal generated during static cone penetration of the sand used in FIG. 7.

FIG. 10 is a chart showing contours of grain size drawn on a plot of r.m.s. voltage of the acoustic signal versus tip resistance at a penetration rate of one centimeter per second.

FIG. 14 is a fragmentary schematic drawing, partly in section of a modified form of penetrometer of this invention.

BRIEF DESCRIPTION OF A PREFERRED EMBODIMENT OF THE PENETROMETER (FIG. 1-6)

Figure 1:
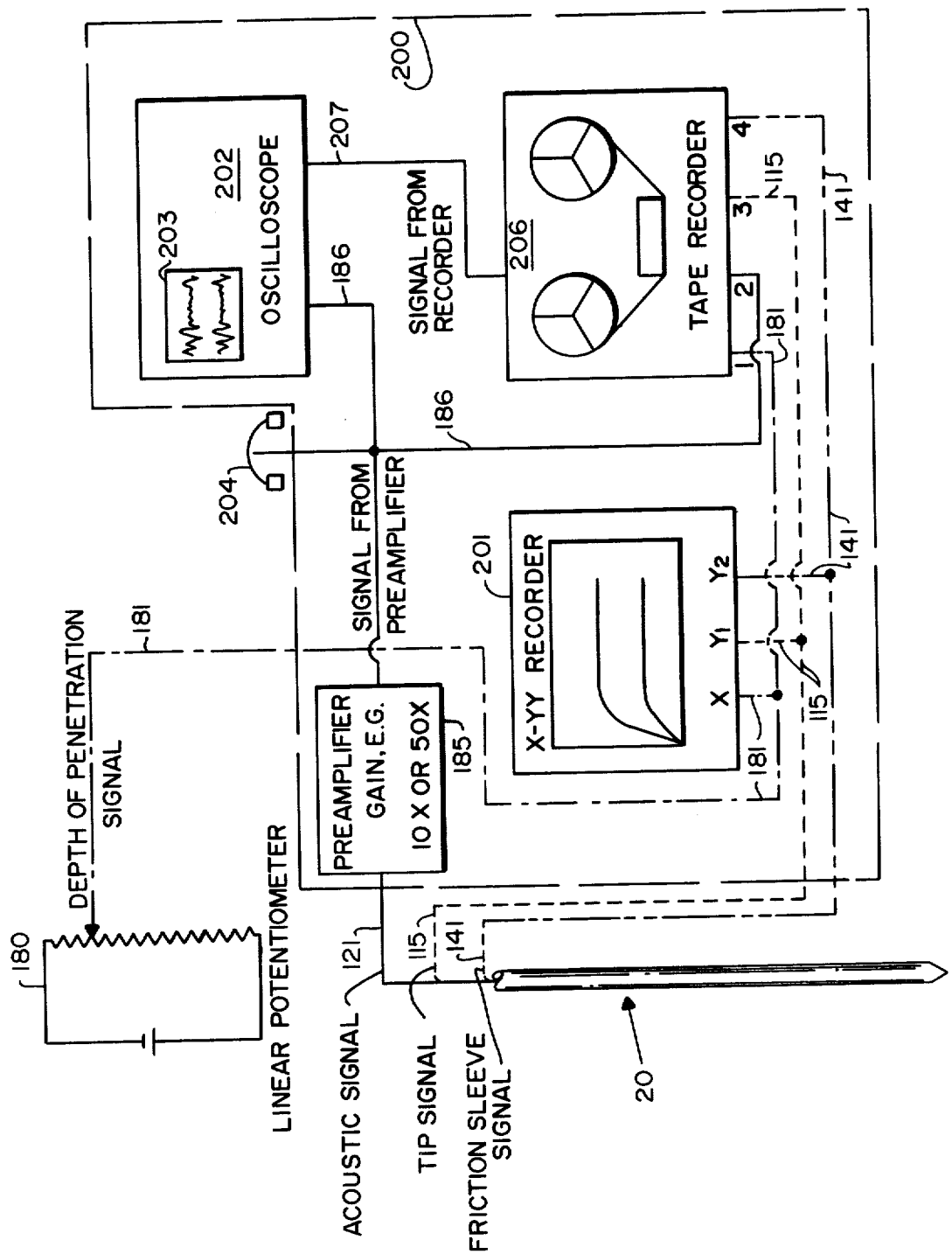
FIG. 1 is a somewhat diagrammatic representation of a system embodying the invention, including a novel penetrometer.
Figure 3:
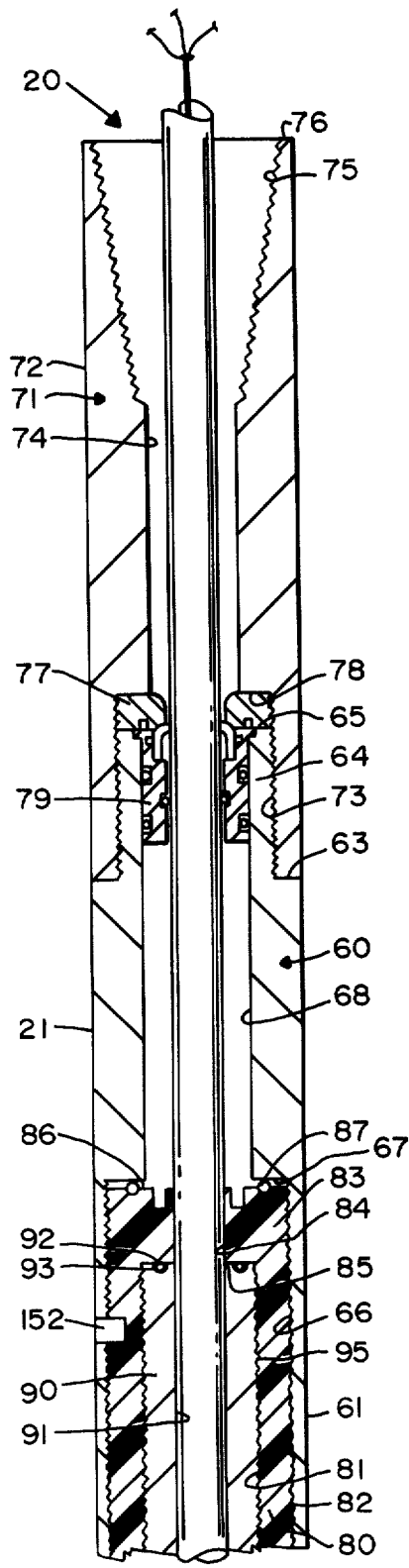
FIG. 3 is a similar view of an upper portion of the same penetrometer.
Figure 2:
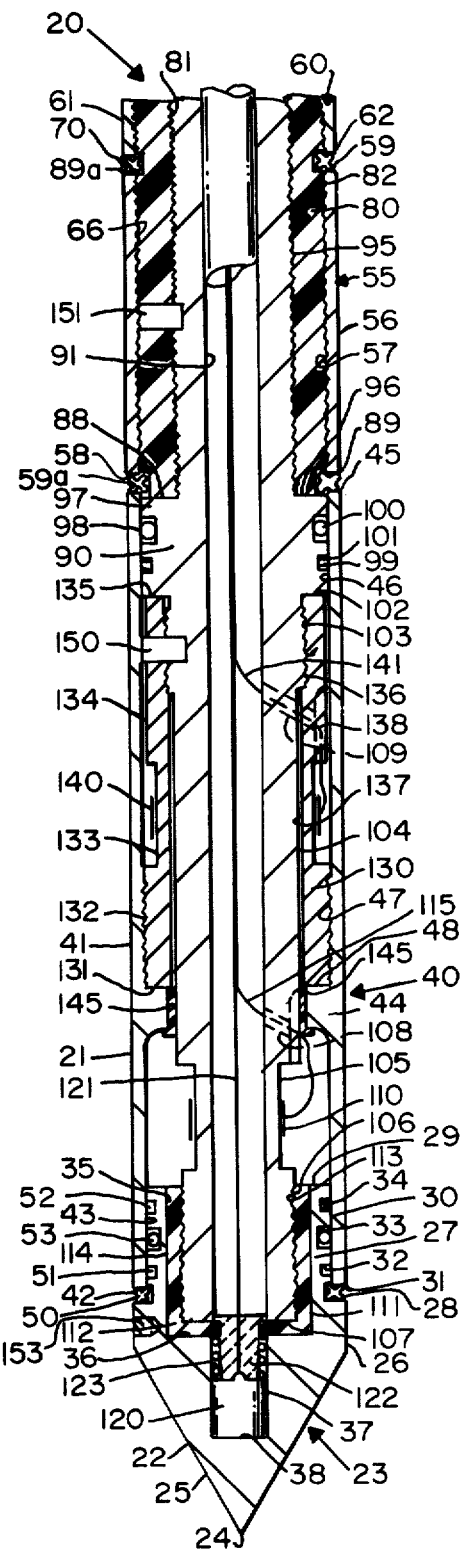
FIG. 2 is a view in vertical cross-section of the lower portion of the penetrometer of FIG. 1.

The invention may be embodied in a quasi-static cone penetrometer 20 which simultaneously generates three sets of data, namely, cone penetration resistance, friction sleeve resistance, and acoustical information, all as a function of depth. The penetrometer 20 has a substantially smooth cylindrical outer surface 21 and terminates in a cone 22 at its lower end.

In its preferred construction, the penetrometer 20 has at its lower end a cone tip member 23 having a 60° cone with a vertex 24 at the bottom end. The tip 23 is preferably of stainless steel. A conical outer surface 25 extends upwardly from the vertex 24 and joins a short smooth cylindrical outer surface 26. The surface 26 may have a diameter of 3.568 cm., so that the cross-sectional area is 10 cm$^2$. An annular portion 27 is inset from the cylindrical outer surface 26 by a shoulder 28 and extends above the shoulder 28 to an upper end 29. The portion 27 has a generally cylindrical outer surface 30 with a series of annular grooves 31, 32, 33 and 34 therein. A cylindrical inner surface 35 leads down from the upper end 29 to an annular shelf 36 just above the height where the short cylindrical outer surface 26 begins, and a central inner well 37 extends down from the shelf 36 to a dead end 38.

Above the cone tip 23 is a friction sleeve 40 preferably of stainless steel, having a smooth cylindrical outer surface 41 of diameter equal to that of the short smooth cylindrical outer surface 26 of the cone tip 23. From a lower end 42 of the sleeve 40, a lower smooth cylindrical inner surface 43 extends up to a guide portion 44 extending inwardly. From an upper end 45 of the friction sleeve 40, an upper smooth cylindrical surface 46 extends down to an interiorly threaded portion 47 and an inwardly projecting shoulder 48 atop the cylindrical guide portion 44.

An elastomeric quad ring 50 is supported by the cone tip 23 in the groove 31 and is compressed between the shoulder 28 of the tip 23 and the lower end 42 of the friction sleeve 40. A pair of Teflon guide rings 51 and 52, seated respectively in the grooves 32 and 34, and an elastomeric O-ring 53 in the groove 33 engage the inner surface 43 of the friction sleeve 40. These rings function as physical separation between the tip 23 and the friction sleeve 40 substantially insulating the tip 23 from the sleeve 40.

Above the friction sleeve 40 is an adjustment sleeve or ring 55, preferably of stainless steel, having a smooth cylindrical outer surface 56 of the same diameter as that of said friction sleeve 40 and cone tip section 26. The ring 55 has a threaded inner surface 57, a lower end 58 and an upper end 59. A second elastomeric quad ring 59a is compressed between the upper end 45 of the friction sleeve 40 and the lower end 58 of the adjustment ring 55.

Above the adjustment ring 55 is an annular adapter rod 60, preferably of stainless steel, having a smooth cylindrical outer surface 61 extending from a lower end 62 up to an upper outer shoulder 63. The rod 60 has an externally threaded upper inset portion 64 above the shoulder 63 terminating in an upper end 65. The rod 60 has an inner threaded portion 66 the same diameter as the inner threaded surface 57 of the adjustment ring 55. This threaded portion 66 extends up from the lower end 62 of the rod 60 to an inner shoulder 67 lying below the outer shoulder 63. This inner shoulder 67 extends inwardly to an inner cylindrical bore 68 that extends up to the top 65 of the rod 60.

A third elastomeric quad ring 70 is compressed between the upper end 59 of the adapter ring 55 and the lower end 62 of the rod 60.

A sounding rod adapter 71, preferably of stainless steel and having a smooth cylindrical surface 72 of the same diameter as that of the rod 60, is connected by an internally threaded portion 73 to the externally threaded portion 64 of the rod 60. The adapter 71 has a smooth bore 74 aligned with the bore 68 of the rod 60. It also has a conically threaded portion 75 at its upper end 76, to which a typical Dutch sounding rod may be fitted. As depths increase beyond the length of the penetrometer, additional Dutch sounding rods are added, using conically threaded joints.

A cable compressing ring 77, preferably of stainless steel, is compressed between a shoulder 78 of the adapter 71 and the upper end 65 of the rod 60. The ring 77 may support a cable compression fitting 79, preferably of stainless steel, with O-rings and rubber seal. The fitting 79 prevents pullout of the cable and wires lying within the penetrometer 20 and coming from the load cells and microphone; it also serves as a primary waterproofing seal for the interior of the penetrometer 20.

An annular dampening member 80 of material such as Delrin has both its inner and outer generally cylindrical surfaces 81 and 82 threaded, except for an inset upper portion 83 with a smooth inner bore 84, a shoulder 85 leading out from the bore 84 to the inner threaded surface 81. The outer surface 82 is threaded to the inner threaded portion 66 of the rod 60 and to the inner threaded surface 57 of the adjustment ring 55. This dampening member 80 has an upper end 86 adjacent to the inner shoulder 67 of the rod 60, and an elastomeric sealing O-ring 87 is compressed between the upper end 86 and the inner shoulder 67. Near the lower end 88 of the member 80 may be a groove 89 supporting the second quad ring 59a. An annular recess 89a similarly supports the third quad ring 70.

An annular core 90 may be made from aluminum and has a smooth inner bore 91 extending through the core. An upper end 92 compresses a sealing O-ring 93 against the shoulder 85 of the dampening member 80 and terminates at its lower end at a radially outwardly extending upper shoulder 96 against which the lower end 88 of the dampening member 80 rests. A short generally cylindrical portion 97 extends down from the shoulder 96 and has annular recesses 98 and 99 in which are an elastomeric sealing O-ring 100 and a Teflon guide ring 101, both bearing against the upper smooth inner cylindrical surface 46 of the friction sleeve 40. A second shoulder 102 therebelow leads into a second outwardly threaded generally cylindrical portion 103. A smooth cylindrical wall 104 therebelow leads down to an inset smooth load cell portion 105, and, below the portion 105, a bottom threaded portion 106 terminates in a lower end 107 of the core 90. The core 90 also has first and second spaced-apart through passages 108 and 109 connecting its inner surface 91 to its outer surface 104.

Tip-responsive strain gauges 110 (four or more to form a load cell) are mounted on the outer surface of the inset portion 105 of said core 90. Their leads 115 pass through the first through passage 108 into the hollow core 91.

A non-metallic acoustical-dampening ring 111 (preferably of Delrin) having a lower inwardly flanged end 112 rests on the shelf 36 of the cone tip 23, preferably partially covering the well 37. The lower end 107 of the core 90 rests on the flange 112. An inner threaded surface 113 of the ring 111 is threaded to the core's bottom threaded portion 106. A smooth outer surface 114 is fixed to the cylindrical inner surface 35 of the tip 23 by means of a suitable adhesive.

A microphone 120 in the well 37 of the tip 23 rests the dead end 38 and has leads 121 extending up through the hollow core 90. The microphone 120 may be of an electret condenser type. Sound barrier material 122 is inserted above the microphone 120. For example, modeling clay may be used. A spring 123 may be used to hold the microphone firmly in place, the spring 123 bearing against the flange 112.

An intermediate sleeve 130 with a lower end 131 resting on the upper end or shoulder 48 of the friction sleeve's guide portion 44 and has a lower outer portion 132 threaded to the threaded portion 47 of the friction sleeve 40. The intermediate sleeve 130 is preferably made from aluminum. An inset load-cell portion 133 lies above the threaded portion 132, and a smooth outer wall 134 above that is spaced radially inwardly from the friction sleeve 40 and leads to an upper end 135 abutting the second shoulder 102 of the core 90. The interior surface of the intermediate sleeve 130 has an upper threaded portion 136 threaded to the second threaded portion 103 of the core 90, and a smooth walled portion 137. A third passage 138 connects the load cell portion 133 to the second passage 109 through the core 90. The interior surface 137 is radially spaced from the core 90 except at the threads 103, 136.

Friction strain gauges 140 (four or more) for friction sleeve measurements are supported on the inset load cell portion 133 of the intermediate sleeve 130, and their leads 141 extend through the third passages 138 and 109 into the hollow core 90.

A guide member 145 of suitable acoustical dampening material, such as Delrin, is interposed between the guide portion 44 of the friction sleeve 40 and the core 90. As a result of the acoustical insulating members 80, 112, 122, and 145, the acoustical system of the microphone 120 is effectively isolated from effects (noise) due to the sleeve 40 as distinct from the acoustical effect at the tip 23.

To retain the parts together, once adjustments have been made, a set screw 150 may be used to lock the intermediate sleeve 130 to the core 90. A setscrew 151 may be used to lock the dampening ring 80 to the core 90, and a set screw 152 may be used to lock the rod 60 to the dampening ring 80. The cone tip 23 may be provided with a filler screw 153 for use with a spanner wrench.

Data Acquisition System (FIG. 1)

Above ground, a linear potentiometer 180 is used to produce a depth-of-penetration signal 181. The acoustic signal from the lead 121 is preamplified (e.g. with a gain of ten times, i.e. 20 dB or fifty times, i.e. 34 dB), by a preamplifier 185 to produce a preamplified signal 186.

A data acquisition system 200, may be housed in a single nineteen inch electronic rack. Preferably, it includes an X-XY recorder 201, used for plotting the tip resistance and the friction sleeve resistance (coming from the penetrometer 20 via the respective leads 115 and 141) versus the depth of penetration signal 181. The system 200 also has a single beam, dual display oscilloscope 202 with a dual display tube 203 to which the preamplified acoustic signal 186 is connected. The signal 186 also goes to a pair of headphone 204 for direct listening to the preamplified acoustic signal 186.

The signal 186 is also sent as one input to a four-channel tape recorder 206, preferably capable of recording both a-c and d-c signals, and the output of the recorded signal may also be sent by lead 207 for display by the oscilloscope 202, in order that the operator may monitor that all is well with the recording process. The four channels of the recorder 206 are utilized respectively, for recording the acoustic signal 186, the depth of penetration information 181, the tip resistance signal 115, and the friction sleeve resistance signal 141. One channel can be temporarily interrupted for voice annotation. The recorder 206 preferably can be slowed down durng playback while retaining full fidelity of the recorded signal. Reducing the tape speed results in a proportional shift in frequency while retaining the true amplitude of the signal. There are two advantages inherent to slowing the tape down during playback: (1) the operator can return to very exact locations on the tape, and (2) view a short period's worth of data over a longer period of time. This provides the opportunity to detect variations in the displayed signal which may be missed in real time.

In addition to the units described above, the rack may contain a patch bay for routing the signals, as well as various power supplies required for operating the load cells. It also may have a bandpass filter with selectable cut-off points, a digital multimeter, and earphones 204 for monitoring the acoustic emissions.

As the penetrometer is advanced into the soil, the grains roll and slide not only over the tip, but also along the friction sleeve and all trailing rods behind the cone—these rods being used for advancing the cone. This in effect means that sound is generated along the entire length of the penetrometer and its associated rods.

If the acoustic sound is to be used to identify thinner layers of soils, then it is important that the sound only be sensed, amplified, listened to, and recorded along a short section of the penetrometer, or even, say a short section of the trailing rods.

There are very definite advantages to having the sound sensitive section within the length of the penetrometer rather than within the rods; penetrometers are frequently advanced until soil resistances reach a value that prohibits further advance. Should the sound sensitive section be within the penetrometer, then it is possible to identify soil layers up to the depth penetrated. If, however, the sound sensitive section is within the rods, then there will exist not only length of rod, but also the penetrometer below the sound sensitive section. For the zone of soil below the sound sensitive section acoustic records will not be available, consequently the usefulness of the measured tip and friction sleeve resistance will be diminished.

The general acoustic penetrometer 220 is shown in FIG. 14. The acoustic penetrometer 220 contains a portion 221 that is exposed to the surface. Within the penetrometer there is an acoustic transducer attached to portion 221 that detects sound caused by soil grains moving over that portion 221. The portion 221 is acoustically isolated from the rest of the penetrometer 220 by acoustic dampening material 222. The penetrometer 220 has a conical tip 223 that has a short section 224 of constant diameter. The tip 223 is conneced to a cone-to-rod adaptor 225 by an internal load measuring means (not shown). The penetrometer 220 also has a friction sleeve 226. This friction sleeve 226 is attached to the cone-to-rod adaptor 225, by an internal load measuring means (not shown). There are sealing rings 227 and 228 between the tip 223 and the friction sleeve 226, and between the friction sleeve 226 and the cone-to-rod adaptor 225 respectively.

The portion 221 sensitive to sound may be located anywhere within the penetrometer 220, i.e. within the tip 223 or within the smooth cylindrical section 229 of the penetrometer 220. If it is within the tip 223, the associated advantages are that tip resistances are measured and acoustic response detected at the same point. If it is elsewhere then the device is easier to fabricate and the sound sensitive portion 221 can be made very small, i.e., it will be possibie to resolve very thin layers of soil.

Penetration tests

Penetration tests have been performed on both wet and dry fabricated soil samples in a controlled environment provided by a large pressure chamber. The chamber was designed to hold a large sample, 800 mm (32 in) in height and 760 mm (30 in) in diameter. The chamber provided independently variable maximum vertical and horizontal stresses—up to 1400 kPa (200 psi) and up to 700 kPa (100 psi) respectively—more than sufficient to simulate stresses at the maximum depths to which static cone penetration tests are performed in the field. The above stresses are equivalent to those existing at a depth of approximately 140 m (460 ft) in a normally consolidated soil with the water table at the ground surface.

Horizontal stresses on the enclosed soil sample were hydraulically applied, while vertical stresses were imposed by eight load transfer rods. In order to prevent vertical stress relaxation as a result of reduction in sample height—which reduction may be caused by compression, consolidation, or creep of the sample—tension on the rods was applied by air pressure.

Sand samples were pluviated so as to maintain selected sample density to within ±8 kg/m$^3$ (½ pcf), corresponding about ±2½ percentage points of relative density for the sand tested. Higher densities are obtained by reducing flow rate or increasing drop height.

The penetration process requires two pieces of equipment; the penetrometer 20 and a drive system for advancing it. A laboratory drive system has been designed to be silent during actual penetration. Due to acoustic attenuation afforded by saturated soils, this precaution is not normally required in the field, where conventional drive systems can consequently be used.

The tone tip 23 used for these tests, having a cross-sectional area of 10 cm$^2$ and a base apex of 60°, contained a miniature elecret condenser microphone 120. The friction sleeve 40, located behind the tip 23 has a surface area of 150 cm$^2$. A penetrometer of this invention has been utilized for a series of penetration tests in a tailings dam. The tip 23, as described above, is acoustically isolated from the trailing friction sleeve 40 and pushrods.

Experimental Procedure

Once a sand sample was consolidated, the penetration tests were performed as follows:
(1) The cone was advanced into the sample at a penetration rate of 1 cm/sec. (0.4 ips) until the tip resistance remained constant. Test results up to this point are ignored.
(2) Five seconds of acoustic data were then recorded at a penetration rate of 1 cm/sec.
(3) Penetration rate was increased to 2 cm/sec (0.8 ips) and a further five seconds of acoustic data were recorded at that rate.
(4) The penetration rate was increased to 4 cm/sec (1.6 ips) and a final 4 seconds worth of acoustic data were recorded.

Analysis of Results

The following results were obtained for each test:
(1) The sample parameters, such as soil type, soil grain characteristics, grain size distribution, void ratio (or relative density), stress state, stress history, and state of saturation.
(2) The cone penetration rate.
(3) The recorded acoustic signal—together with information regarding total gain from the microphone output to tape recorder output.
(4) The tip and friction sleeve resistance data.

These laboratory penetration tests were performed on various gradations of a commercially available windblown dune sand known as Lone Star Lapis Lustre.

Typical tip and friction sleeve resistance data are shown in FIG. 7.

The upper curve is tip resistance, the lower curve, friction sleeve resistance. The rather small variations in tip resistance with penetration depth (from about 130 to 145 kg/cm$^2$) are indicative of a high degree of sample uniformity from top to bottom.

The portions of the above test that were used for the analysis of acoustic results are, for 1, 2 and 4 cm/s respectively;
(1) From a depth of 15.5 to 20 cm.
(2) From 20 to 33.5 cm.
(3) From 33.5 to 50.3 cm.

Subsequent to the conclusion of a test, the acoustic signals were evaluated and analayzed by:
(1) Display on the oscilloscope.
(2) Determination of the rms voltage of the recorded signal.
(3) Frequency distribution analysis.
(4) Listening to the recorded signal.

The primary reason for displaying the signal on the oscilloscope was to ensure that peak-to-peak amplitude did not vary with time, as such variation would have rendered meaningless the averaging during the frequency distribution analyses.

In the laboratory, rms voltage was determined by means of a digital multimeter. In the field, where rms voltage of the acoustic signal varies with geologic layering, this method is not practical. In that environment, either peak-to-peak, or rms, voltage can be plotted (in real time) as a function of depth of penetration by means of either a peak, or true rms, voltage detector.

The frequency distribution analysis was performed by means of a digital, real time, Fast Fourier Transform (FFT) analyzer.

The recorded signal was played back into the analyzer. A short segment of the signal, referred to as a time window or sample, was digitized and cosine tapered. By means of Fast Fourier analysis, the amplitude versus frequency distribution of that sample (time window) was determined. The amplitude was divided by the preselected number of time windows to be analyzed, and the resultant frequency distribution curve was stored in a memory. The process was repeated with a next time window, with the resultant curve beng added to the one already in the memory. When the selected number of time windows had been analyzed, the final frequency distribution curve, in the memory, was displayed on a cathode ray tube and plotted. An example of the resulting frequency distribution curve is shown in FIG. 8. The curve shows rms voltage as a function of frequency from 0 Hz to 20 kHz.

Note that the amplitude is referred to as amplitude at the microphone. As a result of the limited dynamic range of electronic instruments, amplification of the acoustic signal varies from test to test, and even for the various penetration rates within a given test. Such amplification was controlled at two points: the gain-setting of the preamplifier, and the sensitivity setting of the tape recorder. In order for the results of various tests to be comparable, all data were converted to the amplitude at the microphone. This was accomplished by dividing the amplitude of the recorded signal by the total gain in the recording chain.

The acoustic signal was also listened to. The human ear is known to be a very discriminating "instrument" with a frequency response from 20 Hz to 20 kHz and a relatively large dynamic range of 130 dB from the threshold of hearing to the threshold of pain.

Figure 9:
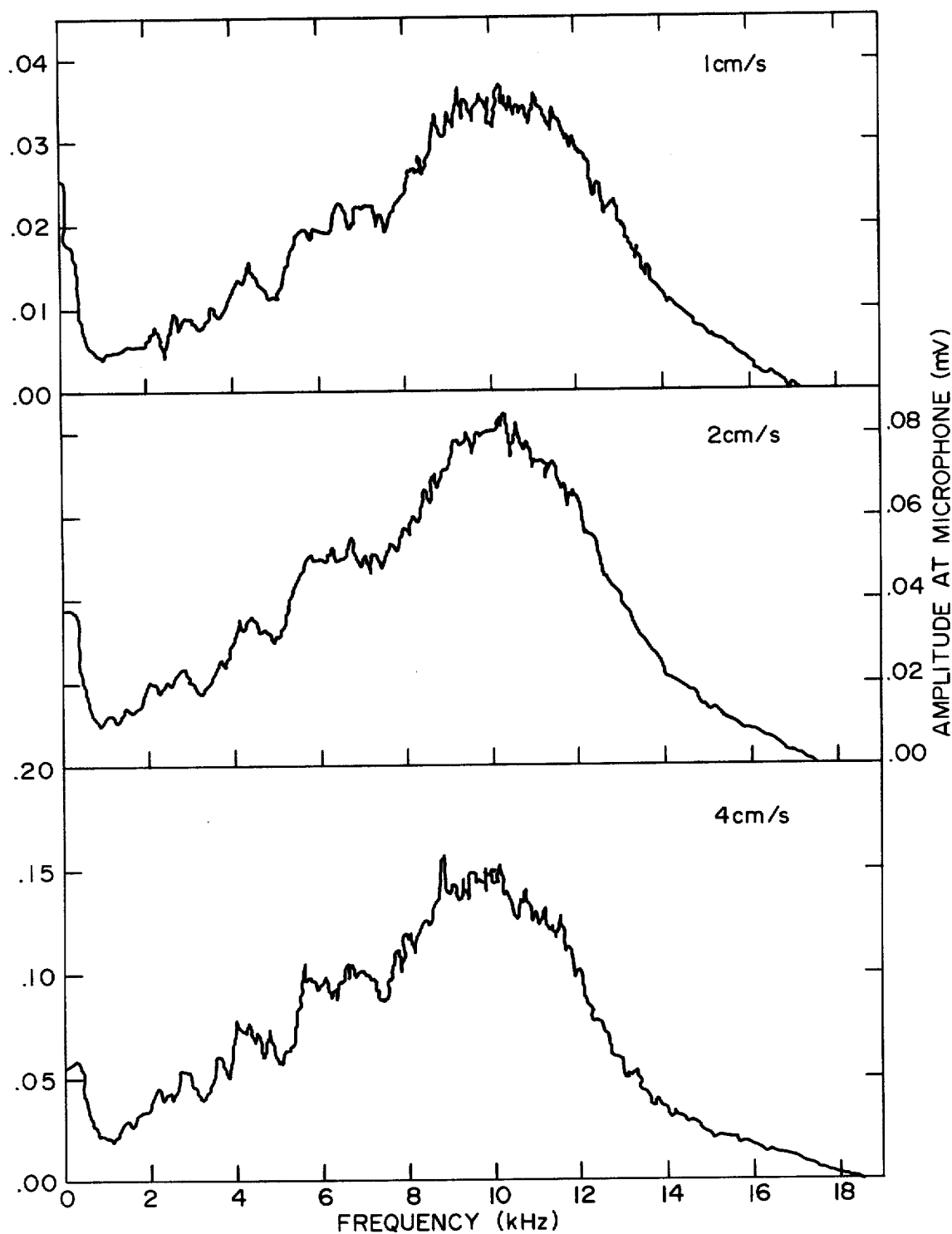
FIG. 9 is a set of three frequency distribution curves obtained at penetration rates of 1, 2, and 4 cm./sec., respectively, reading from top to bottom, employing vertical scales expanded a different amount for the inspection tests.

Each complete test yielded three frequency distribution curves, one for each of the selected penetration rates. FIG. 9 shows the frequency distribution curves obtained in one such test, at penetration rates of 1, 2, and 4 cm/sec.

Note that the vertical scales for the three curves in FIG. 9 are not identical, but have been expanded to illustrate the general shape of each curve. Other than amplitude variations, the patterns of the curves obtained at the three penetration rates are remarkably similar. A major peak exists around 6 kHz, with secondary peaks shown at 2.5 and 4.5. The peak at 0.5 kHz has been found to be due to electric and mechanical noise in the testing environment.

The results of the tests described above showed that:
(1) By means of a simple root mean square voltage measurement of the amplitude of the acoustic signal it is possible to predict the average grain size, $D_{50}$, of the tested sands with a certainty of plus or minus 5 percent.
(2) The tip resistance measured in this study, in conjunction with tip resistance measured by other researchers, have indicated that a unique relationship among tip resistance, relative density and confining stress, valid for all sands does not exist. The results do, however, show that it is possible to develop such relationships for any sand if sand type is taken into account, either directly by measurement of its friction angle, or indirectly by grain size and gradation.
(3) The grain size information required to interpret static cone penetration tests satisfactorily can be provided by the analysis of the acoustic emissions generated during the static cone penetration of sands, as shown for penetration rates of 1, 2 and 4 cm/sec. in FIGS. 10, 11 and 12.

The effects of sress history on (1) the acoustic signal and (2) the measured resistances were evaluated by testing overconsolidated sand samples.

Well graded sand was tested under saturated normally consolidated conditions.

The ratio of horizontal to vertical stress for nearly all normally consolidated samples was 0.5. In the expanded test series for the medium uniform gradation, a few samples were tested where the ratio was 0.33. For overconsolidated samples, the ratio varied between0.75 and 1.0.

Penetration tests were performed on the fabricated samples by initially advancing the cone into the sample at a rate of 1 cm/s. Once the tip resistance reached a plateau value, the cone was stopped. Results up to this point were ignored. The cone was then advanced for 5 cm at a a penetration rate of 1 cm/s. Penetration rate increased to 2 cm/s, and an additional 10 cm of the sample penetrated. A final 16 cm section of the sample was penetrated at 4 cm/s.

The recorded acoustic signals were analyzed by: (1) measuring their root means square voltage, and (2) frequency distribution analysis.

The frequency distribution curves obtained in the various gradations, at penetration rates of 1, 2 and 4 cm/s are remarkably similar in general shape, with dominant peaks in the 6 to 8 kHz range, for all tests where the cone tip was not filled with hydraulic fluid. There are, however, very pronounced differences in amplitudes, as indicated by both rms voltage measurements and the frequency distribution curves.

Rms voltages of the acoustic signal were measured with frequencies below 1 kHz filtered out of the signal, as penetration tests in air, and subsequent frequency distribution analysis showed the energy below 1 kHz to be mainly electrical and mechanical noise.

The rms voltages and frequency distribution curves show the following trends:
(1) In a given sample, the amplitude of the acoustic signal increases linearly with penetration rate for the rates used (1 to 4 cm/s).
(2) For a given sand of a given relative density, and at a given confining stress, amplitudes are higher in dry than in saturated samples by at least a factor of two.
(3) For a given sand, at a given penetration rate, amplitude decreases with increasing penetration resistance. This trend diminishes as grain size decreases, and was nearly nonexistent for the finest uniform gradation.
(4) The trend mentioned in (3) above is, however, small in comparison to the increase in amplitude, at a given penetration rate, with increasing grain size. The rms voltages measured at a given penetration rate in the medium sand are all higher than those measured in the fine sand, while the voltages measured in the coarse sand are higher than those measured in the medium sand.
(5) If rms voltage at a given penetration rate is plotted against tip resistance, it is possible to construct contours of average grain size. Such contours should enable the prediction of average grain sizes in the field on the basis of rms voltages of the acoustic signal and measured tip resistances.

These contours of grain size do not seem to be sensitive to eigher variations in gradation uniformity or to stress history. Although the contours were constructed with the voltages and tip resistances measured in the uniformly graded samples, when the voltages and tip resistances measured in the mixed, less uniform sand were plotted, the known average grain size of the mixture (0.46 mm) was within 5 percent of the values indicated by the grain size contours.

(6) The frequency distribution curves show that there is a slight tendency for dominant frequency to decrease with increasing penetration resistance. The frequency distribution curves seem to indicate different failure modes at different tip resistances, as indicated by the changes in the curves with increasing tip resistance.

An important conclusion that can be drawn from the above trends is that the evaluation of the acoustic signal enables the accurate determination of grain size on the basis of a relatively simple measurement of rms voltage. If the method can (as has been shown) distinguish reliably between sands with average grain sizes differing as little as 0.30, 0.39 and 0.46 mm, then it will be a very reliable indicator of soil type. Other conclusions relating to the acoustic response include: (1) In a given soil layer the amplitude of the acoutic signal will decrease as the water table is crossed, thus enabling the location of the water table. (2) The stong dependence of amplitude on penetration rate suggests that penetration rate has to be very exactly controlled, or measured, if amplitudes are to be meaningfully interpreted in quasistatic cone penetration tests. It appears that the amplitude of the acoustic signal in a given soil layer can be used as a means for measuring variations in penetrometer velocity. This is relevant to the analysis associated with free falling penetrometers, such as used in the offshore environment, and also to the analysis of the results obtained with dynamic impact penetrometers such as used in the standard penetration test (SPT).

The tip resistances measured in this study were relatively constant in a given sample irrespective of penetration rate. Tip resistance increased with relative density and with confining stress. At a given relative density and confining stress, tip resistances measured in the finer and medium uniform gradations, as well as in the mixed sand, were approximately the same. Tip resistances measured in the coarser sand, at the same relative density and confining stress, were higher than for the other sands.

The tip resistance, relative density, confining stress relationships established in this study showed trends similar to some previously published. At a given stress and relative density, tip resistances measured in this study were, however, substantially higher than previously published relationships would indicate. These differences were as large as a factor of two.

This research also showed that the relationships among tip resistance, stress, and relative density could be predicted provided that sand types were taken into account, either directly by measurement of their friction angles or indirectly from information pertaining to grain size.

It appears that the evaluation of the acoustic signal generated during the static penetration of soils can yield the required information, and thus greatly enhance the certainty with which penetration records can be interpreted.

Field tests

Series of field tests were performed on a tailings dam in British Columbia and at four geologically different sites in California.

Figure 13:
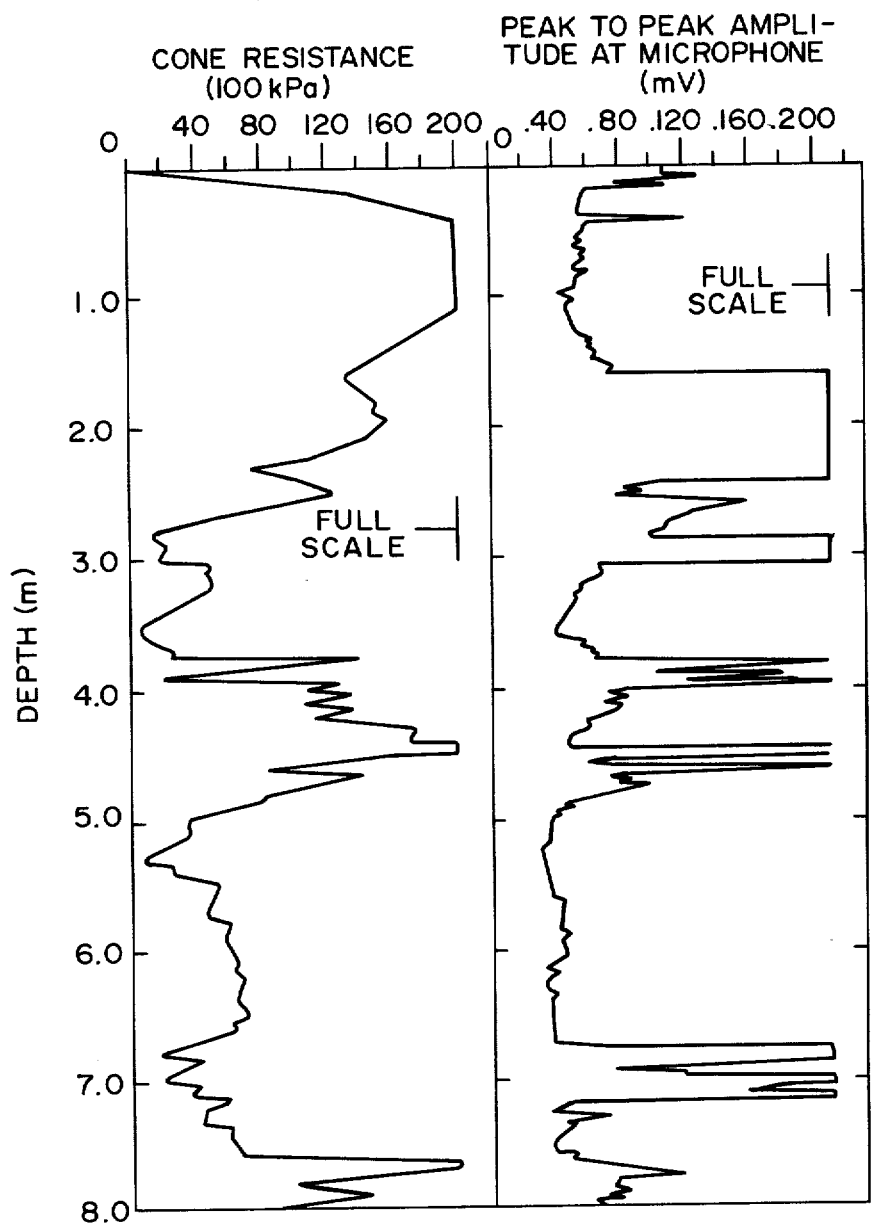
FIG. 13 is a chart of cone-tip resistances and peak-to-peak voltages of the acoustic signal as a function of depth of penetration.

Data obtained at a penetration rate of 4 cm/sec. in one of the field tests in British Columbia are shown in FIG. 13. Tip resistance, as well as peak-to-peak voltage of the generated acoustic signal, are plotted as a function of depth of penetration.

Both tip resistance and the peak-to-peak voltage clearly indicate layering; below a depth of 1.7 m the higher amplitude acoustic signals can be seen to correspond to zones of higher tip resistance. At a depth of about seven meters a high amplitude acoustic signal was generated, although tip resistance remained low.

Sand particle sizes

Figure 11:
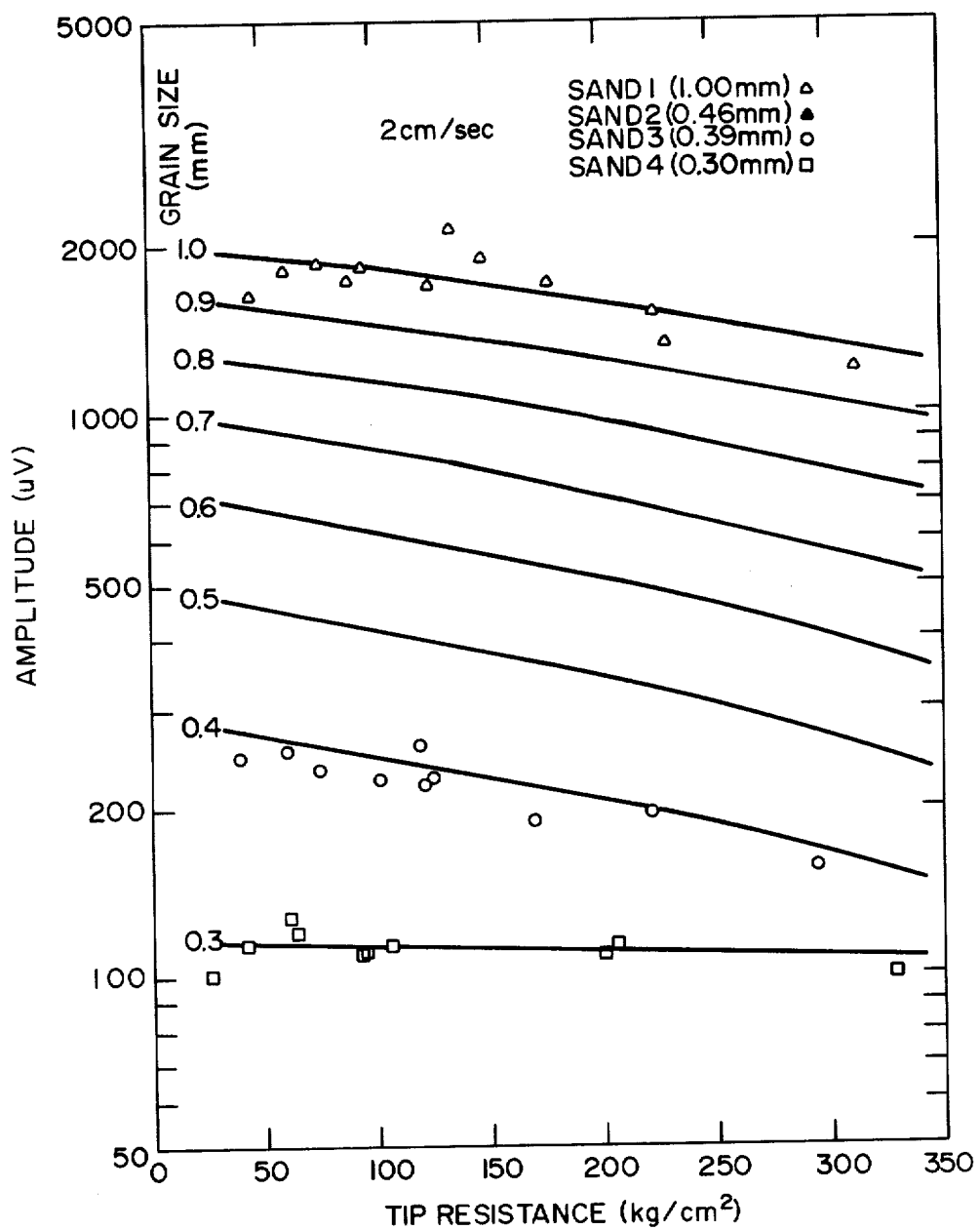
FIG. 11 is a similar chart with values obtained at a penetration rate of two centimeters per second.
Figure 12:
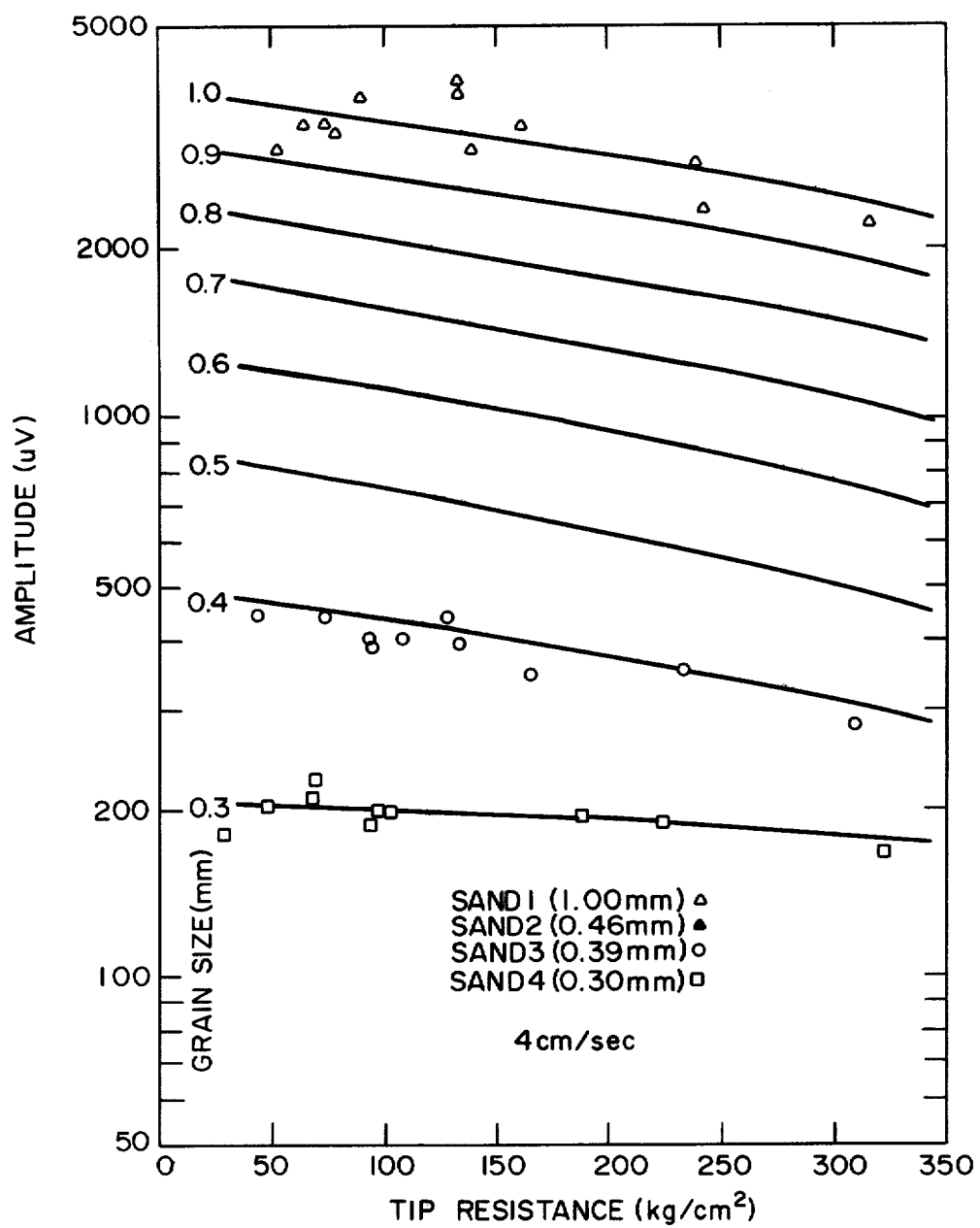
FIG. 12 is another similar chart with values obtained at a penetration rate of four centimeters per second.

FIGS. 10 to 12 show how well actual grain size of sands corresponds with the correlation between tip resistance and acoustical amplitude.

For these tests, four uniform gradations of Monterey Sand—a soil composed of subrounded to subangular quartz and feldspar grains—were tested.

Sand 1 had a grain size of 1.0 mm, Sand 2 a grain size of 0.46 mm, Sand 3 a grain size of 0.39 mm, and Sand 4 a size of 0.30 mm. In each case they correspond clearly to the contour of grain size on the plot of acoustical amplitude versus tip resistance. Another gradation was obtained by mixing the first, second and fourth sands in equal mass proportions. The relationship holds for penetration rates of 1 cm/sec. (FIG. 10), 2cm/sec. (FIG. 11), and 3 cm/sec. (FIG. 12).

Thus the acoustical information can, by the penetrometer of this invention, give the grain sizes of materials well down in the subsoil.

The data for these charts were obtained by static cone penetration tests performed in a large triaxial cell with an acoustic cone penetrometer of this invention. The triaxial cell had independently variable horizontal and vertical stresses with maximum possible values of 700 kPa and 1400 kPa respectively. Sample dimensions were 800 mm in height and 760 mm in diameter. The samples were reproducible, being performed by pluviation.

Saturated samples of the uniform gradations were tested under the stress and relative density conditions shown in Table A. At least one dry sample of each uniform gradation was also tested at one of the Table A matrix points.

TABLE A

| Idealized test conditions for each sand. | | | |
|---|---|---|---|
| Relative Density in % | Vertical Stress During Testing in kPa | | |
| 25 | 70 | 140 | 280 |
| 50 | 70 | 140 | 280 |
| 75 | 70 | 140 | 280 |

The medium uniform gradation was extensively tested under additional stress and relative density conditions.

To those skilled in the art to which this invention relates, many changes in construction and widely differing embodiments and application of the invention will suggest themselves without departing from the spirit and scope of the invention. The disclosures and the descriptions herein are purely illustrative and are not intended to be in any sense limiting.

We claim:

1. A quasi-static cone penetrometer for subsoil investigation by simultaneously generating three sets of data, namely cone tip penetration resistance, friction sleeve resistance, and acoustical information, all as a function of depth, said penetrometer comprising a body assembly with a substantially cylindrical outer surface and terminating in a cone at its lower end, said body assembly having a cone tip, a friction sleeve above said cone tip, propelling means for advancing said body assembly into soil, first load-responsive means connected to said tip, for measuring tip load, second load-responsive means connected to said friction sleeve, for determining friction sleeve load, said first and second load responsive means extending through said rod means, an acoustic transducer in contact with an area of said body assembly responsive to acoustical input generated by the body assembly moving through the soil, and a lead from said acoustical transducer, extending up through said body assembly to the upper end of said penetrometer.

2. The penetrometer of claim 1 wherein said acoustic transducer is located in contact with said cone tip.

3. The penetrometer of claim 1 wherein said acoustic transducer is located in contact with a cylindrical surface of said body assembly.

4. A quasi-static cone penetrometer for subsoil investigation by simultaneously generating three sets of data, namely cone tip penetration resistance, friction sleeve resistance, and acoustical information, all as a function of depth, said penetrometer comprising a body assembly with a substantially smooth cylindrical outer surface and terminating in a cone at its lower end, said body assembly having a cone tip, a friction sleeve immediately above said cone tip, with an outer surface forming part of said smooth cylindrical outer surface, rod means for advancing said body assembly into soil, a tip load cell joined to said tip, a friction load cell joined to said friction sleeve, said friction load cell and said tip load cell being joined to said rod means.

an acoustic transducer in contact with said tip responsive to acoustical input generated by the tip moving through the soil, and leads from each of said load cells and from said acoustical transducer, extending up through said body assembly to the upper end of said penetrometer.

5. The penetrometer of claim 4 having acoustic dampening means between the two said load cells and between each load cell and the acoustic transducer.

6. A quasi-static cone penetrometer for subsoil investigation by simultaneously generating three sets of data, namely cone tip penetration resistance, friction sleeve resistance, and acoustical information, all as a function of depth, said penetrometer comprising a body assembly with a substantially cylindrical outer surface and terminating in a cone at its lower end, said body assembly having a cone tip, a friction sleeve immediately above said cone tip, with an outer surface forming part of said cylindrical outer surface, said surface having an annular recess therein, rod means for advancing said body assembly into soil, a tip load cell joined to said tip, a friction load cell joined to said friction sleeve, said friction load cell and said tip load cell being joined to said rod means, an acoustic transducer in said annular recess and insulated from said friction sleeve, responsive to acoustical input generated by the sleeve moving through the soil, and leads from each of said load cells and from said acoustical transducer, extending up through said body assembly to the upper end of said penetrometer.

7. A quasi-static cone penetrometer for subsoil investigation by simultaneously generating three sets of data, namely cone tip penetration resistance, friction sleeve resistance, and acoustical information, all as a function of depth, said penetrometer comprising a body assembly with a substantially smooth cylindrical outer surface and terminating in a cone at its lower end, said body assembly having a cone tip, a friction sleeve immediately above said cone tip, with an outer surface forming part of said smooth cylindrical outer surface, acoustic attenuation means between said cone tip member and said friction sleeve for substantially insulating them acoustically from each other, a tip load cell having an inner bore, acoustical-dampening means interposed between said cone tip and said tip load cell for joining them while insulating them acoustically from each other while transmitting to said tip load cell the resistance of the soil to the movement of said cone tip thereinto, an annular friction load cell around said tip load cell and within said friction sleeve, with an upper end connected to said tip load cell while the remainder is spaced away from it and a lower end secured to said friction sleeve, a microphone in said tip responsive to acoustical input generated by the tip moving through the soil, sound barrier means holding said microphone firmly in place in said tip, said sound barrier means, said acoustic attenuation means, and said acoustical dampening means substantially isolating said microphone from said tip load cell and from said friction sleeve, and leads from each of said load cells and from said microphone, extending up through said bore to the upper end of said penetrometer.

8. The penetrometer of claim 7 wherein said body assembly includes additional shell portions continuing said smooth cylindrical outer surface upwardly from said friction sleeve and an annular accoustical dampening member interposed between said shell portions and said tip load cell.

9. The penetrometer of claim 8 wherein said annular acoustical dampening member is threaded to said shell portions and to said tip load cell.

10. The penetrometer of claim 7 wherein said cone tip has a central interior well axially in line with said vertex, and a shelf therearound and thereabove, said acoustical dampening means is a non-metallic acoustical-dampening ring having a lower inwardly flanged end resting on said shelf of said core tip and on which the lower end of said tip load cell rests, said tip load cell being rigidly secured to said dampening ring, said microphone being held in said well by said sound barrier material.

11. The penetrometer of claim 10 wherein said acoustical dampening ring is threaded to said tip load cell.

12. The penetrometer of claim 7 wherein said cone tip has a reduced-diameter upper portion extending up inside said friction sleeve and said acoustic attenuation means includes a plurality of non-metallic rings retained by said upper portion and in contact with the interior surface of said friction sleeve.

13. A quasi-static cone penetrometer for subsoil investigation by simultaneously generating three sets of data, namely cone tip penetration resistance, friction sleeve resistance, and acoustical information, said penetrometer comprising a body assembly with a substantially smooth cylindrical outer surface and terminating in a cone at its lower end, said body assembly having a cone tip member having a cone vertex at the bottom end and a conical outer surface extending upwardly from the vertex to said smooth cylindrical outer surface, a friction sleeve immediately above said cone tip and having an outer surface forming part of said smooth cylindrical outer surface, acoustic attenuation means between said cone tip member and said friction sleeve for substantially insulating them acoustically from each other, a core ring having an inner bore and a load cell portion with a tip-responsive strain gauge mounted thereto, acoustical-dampening means interposed between said cone tip member and said core ring for insulating them acoustically from each other while transmitting to said strain gauge the resistance of the soil to the movement of the tip thereinto, an intermediate friction load cell sleeve around said core ring with its upper end connected to said core ring and the remainder spaced away from it and its lower end secured to said friction sleeve, said intermediate sleeve having a load cell portion with a friction strain gauge for sleeve friction measurement, supported thereon and responsive to the friction of said friction sleeve relative to the soil, a microphone in said tip responsive to acoustical input generated by the tip moving through the soil, sound barrier means holding said microphone firmly in place in said tip, said sound barrier means, said acoustic attenuation means, and said acoustical dampening means substantially isolating said microphone from said core ring and said friction sleeve, and leads from each of said straing gauges and from said microphone, extending up through said bore to the upper end of said penetrometer.

14. The penetrometer of claim 13 wherein said body assembly includes additional shell portions continuing said smooth cylindrical outer surface upwardly from said friction sleeve and an annular acoustical dampening member interposed between said shell portions and said core ring.

15. A quasi static cone penetrometer system for subsoil investigation by simultaneously generating three sets of data, namely cone tip penetration resistance, friction sleeve resistance, and acoustical information, all as a function of depth, said penetrometer comprising a body assembly with a substantially smooth cylindrical outer surface and terminating in a cone at its lower end, said body assembly having a cone tip, a friction sleeve immediately above said cone tip, with an outer surface forming part of said smooth cylindrical outer surface, rod means for advancing said body assembly into soil, a tip load cell joined to said tip, a friction load cell joined to said friction sleeve, said friction load cell and said tip load cell being joined to said rod means, an acoustic transducer in contact with said tip responsive to acoustical input generated by the tip moving through the soil, leads from each of said load cells and from said acoustical transducer, extending up through said body assembly to the upper end of said penetrometer and thence to ground level, a preamplifier at ground level connected to the lead from said acoustical transducer for amplifying the signal therefrom, a linear potentiometer at ground level connected to said penetrometer for developing a depth of penetration signal and having a lead for carrying that signal, an X-YY recorder at ground level connected to the lead from said potentiometer and to the leads from each said load cell, and signal recording means for simultaneously recording on a single medium the signals from each said load cell, said acoustic transducer preamplifier, and said potentiometer.

16. The system of claim 15 having also an oscilloscope connected to said preamplifier output and to said tape recorder's acoustic input for comparing the acoustic signals.

17. The system of claim 15 having earphones connected to said preamplifier output for listening directly to the preamplified acoustic signal.

18. A method of subsoil investigation to determine the engineering properties of various soil, comprising driving into the subsoil at a constant rate of speed a penetrometer having a cone tip with a microphone therein and a friction sleeve, while simultaneously generating electric signals corresponding to cone tip resistance, friction sleeve resistance, and sounds resulting from the soil grains near the cone tip sliding and rolling over one another and sliding and rolling over the penetrometer cone tip, and while also simultaneously generating a depth-of-penetration signal coresponding to the depth of the cone tip, transmitting the four resulting signals to a data acquisition system, utilizing the sounds signal obtained from the subsoil in conjunction with the depth-of-penetration signal to determine the grain size at each depth, and then utilizing the grain size information and the tip and friction sleeve resistances to determine engineering properties of the soil.

19. The method of claim 18 including listening to said sounds directly while observing at least one of the other signals.

20. A method of subsoil investigation to determine the engineering properties of various soil, comprising driving into the subsoil at a constant rate of speed a penetrometer having a cone tip with a microphone therein and a friction sleeve, while simultaneously generating electric signals corresponding to cone tip resistance, friction sleeve resistance, and sounds resulting from the soil grains near the cone tip sliding and rolling over one another and sliding and rolling over the penetrometer cone tip, and while also simultaneously generating a depth-of-penetration signal corresponding to the depth of the cone tip, transmitting the four resulting signals to a data acquisition system, and recording the four signals simultaneously on recording medium.

21. The method of claim 20 wherein the four signals are recorded on a single tape.

22. The method of claim 20 including displaying the signals while they are being recorded and simultaneously listening to said sounds.

* * * * *